(12) United States Patent
Awaad et al.

(10) Patent No.: US 10,016,425 B2
(45) Date of Patent: Jul. 10, 2018

(54) ANTI-ULCERATIVE COLITIS COMPOUND

(71) Applicant: KING SAUD UNIVERSITY, Riyadh (SA)

(72) Inventors: Amani Shafeek Awaad, Riyadh (SA); Ahmed Mahmoud Ahmed Alafify, Riyadh (SA); Reham Mostafa El-Meligy, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/343,154

(22) Filed: Nov. 3, 2016

(65) Prior Publication Data

US 2018/0117046 A1 May 3, 2018

(51) Int. Cl.
 *A61K 31/517* (2006.01)
 *A61K 9/00* (2006.01)

(52) U.S. Cl.
 CPC .......... *A61K 31/517* (2013.01); *A61K 9/0053* (2013.01)

(58) Field of Classification Search
 CPC .................................................. A61K 31/517
 See application file for complete search history.

(56) References Cited

U.S. PATENT DOCUMENTS

| | | | |
|---|---|---|---|
| 6,184,226 B1 | 2/2001 | Chakravarty et al. | |
| 7,829,708 B2 | 11/2010 | Roberts et al. | |
| 7,960,399 B2 | 6/2011 | Ritchie | |
| 8,440,677 B2 | 5/2013 | Evarts et al. | |
| 2006/0111376 A1 | 5/2006 | Hallberg et al. | |
| 2009/0035306 A1* | 2/2009 | Pinkerton ............ | A61K 31/517 424/133.1 |

FOREIGN PATENT DOCUMENTS

| | | |
|---|---|---|
| WO | WO 97/02254 A1 | 1/1997 |
| WO | WO 2010/146173 A1 | 12/2010 |

OTHER PUBLICATIONS

Alafeefy et al., Journal of Enzyme Inhibition and Medicinal Chemistry (2015), 30(2), 270-276.*
Wang et al., "Quinazoline derivatives: synthesis and bioactivities," Chemistry Central Journal, 2013, vol. 7, pp. 1-15.
Parmar et al., "Design, Synthesis and Biological Screening of Novel 3-Amino Quinazolines as Antiulcer Agents," JPSBR, 2014, vol. 4, pp. 286-292.

* cited by examiner

*Primary Examiner* — Paul V Ward
(74) *Attorney, Agent, or Firm* — Richard C. Litman

(57) ABSTRACT

Anti-ulcerative colitis compounds include quinazoline derivatives having the following structural formula:

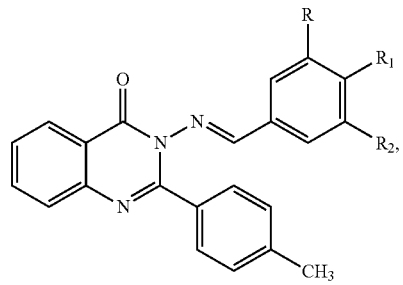

wherein R is H, OH, or $OCH_3$, $R_1$ is OH or $OCH_3$, and $R_2$ is $OCH_3$ or a pharmaceutically acceptable salt thereof.

8 Claims, No Drawings

ANTI-ULCERATIVE COLITIS COMPOUND

BACKGROUND OF THE INVENTION

1. Field of the Invention

The present invention relates to the treatment of ulcerative colitis, and particularly, to a quinazoline derivative for the treatment of ulcerative colitis.

2. Description of the Related Art

Ulcerative colitis (UC) is a form of inflammatory bowel disease (IBD) that primarily affects the colonic mucosa. Aminosalicylates are the primary anti-inflammatory drugs used to treat ulcerative colitis. The anti-inflammatory action in aminosalicylates is produced by 5-aminosalicylic acid (5-ASA), however 5-ASA is poorly-absorbed by the intestines, thus providing only topical relief within the intestine; i.e., aminosalicylates are non-systemic drugs. Additionally, the side-effects of 5-ASA include nausea and vomiting, reduced sperm count and damage to red or white blood cells, or to the liver, kidneys, pancreas, nerves or hearing.

Given the side effects of many primary treatments for ulcerative colitis, it would be desirable to develop a treatment which avoids or minimizes such potential effects. Thus, an anti-ulcerative colitis compound solving the aforementioned problems is desired.

SUMMARY OF THE INVENTION

The anti-ulcerative colitis compound is a quinazoline derivative, having the structural formula:

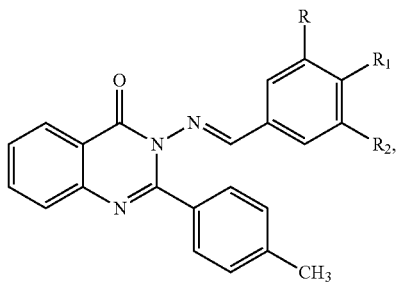

wherein R is H or $OCH_3$, $R_1$ is OH or $OCH_3$, and $R_2$ is $OCH_3$. or a pharmaceutically acceptable salt thereof.

An exemplary anti-ulcerative colitis compound is 3-[(4-hydroxy-3-methoxy-benzylidene)-amino]-2-p-tolyl-3H-quinazolin-4-one, having the following chemical structure:

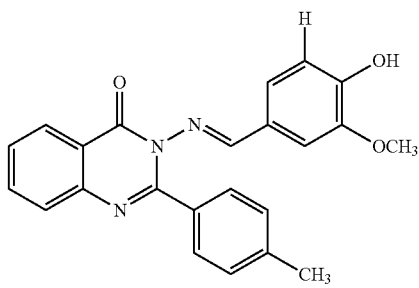 [SMILES: COc1cc(/C=N/n2c(-c3ccc(C)cc3)nc3ccccc3c2=O)ccc1O]

or a pharmaceutically acceptable salt thereof.

Another exemplary anti-ulcerative colitis compound is 2-p-tolyl-3-[3,4,5-trimethoxy-benzylidene-amino]-3H-quinazolin-4-one, having the following chemical structure:

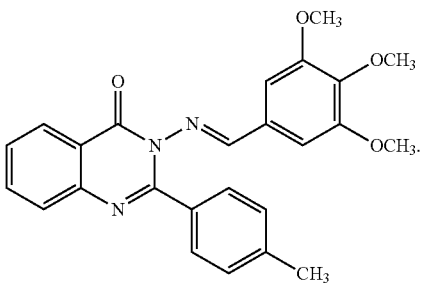 [SMILES: COc1cc(/C=N/n2c(-c3ccc(C)cc3)nc3ccccc3c2=O)cc(OC)c1OC]

These and other features of the present invention will become readily apparent upon further review of the following specification.

DETAILED DESCRIPTION OF THE PREFERRED EMBODIMENTS

Anti-ulcerative colitis compounds include quinazoline derivatives having the following structural formula:

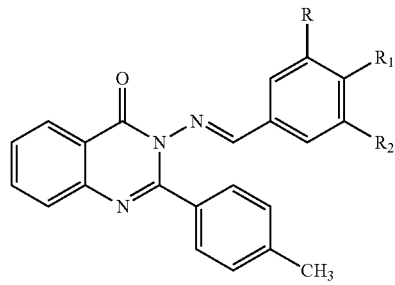

wherein R is H or $OCH_3$, $R_1$ is OH or $OCH_3$ and $R_2$ is $OCH_3$, or a pharmaceutically acceptable salt thereof.

An exemplary anti-ulcerative colitis compound is 3-[(4-hydroxy-3-methoxy-benzylidene)-amino]-2-p-tolyl-3H-quinazolin-4-one (Compound 5), having the following chemical structure:

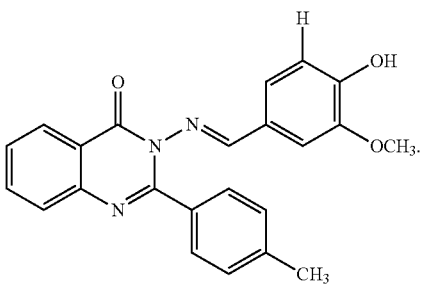 [SMILES: COc1cc(/C=N/n2c(-c3ccc(C)cc3)nc3ccccc3c2=O)ccc1O]

Another exemplary anti-ulcerative colitis compound is 2-p-tolyl-3-[3,4,5-trimethoxy-benzylidene-amino]-3H-quinazolin-4-one, having the following chemical structure:

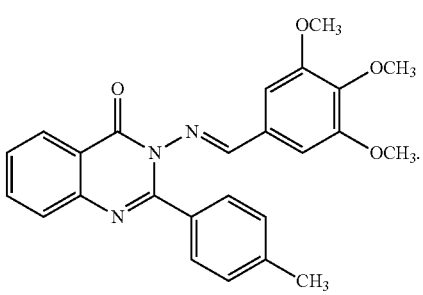 [SMILES: COc1cc(/C=N/n2c(-c3ccc(C)cc3)nc3ccccc3c2=O)cc(OC)c1OC]

An exemplary method for synthesizing the anti-ulcerative colitis compounds includes reacting anthranilic acid with 4-toluoyl chloride to form a first solution; evaporating a solvent from the first solution to yield 2-(4-methylbenzamido)benzoic acid; refluxing the 2-(4-methylbenzamido) benzoic acid with acetic anhydride to yield 2-p-tolyl-4H-3,1-benzoxazin-4-one; boiling the 2-p-tolyl-4H-3,1-benzoxazin-4-one with hydrazine hydrate in the presence of absolute ethanol to produce 2-(4-methylphenyl)-3-amino-3H-quinazolin-4-one; and treating the 2-(4-methylphenyl)-3-amino-3H-quinazolin-4-one with an aldehyde derivative to produce the anti-ulcerative colitis compound. For example, a mixture of 2-(4-methylphenyl)-3-amino-3H-quinazolin-4-one and an appropriate aldehyde can be heated in acetic acid under reflux. The aldehyde derivative can include vanillin and/or 3,4,5-trimethoxy-benzaldehyde, and the mixture can be heated for about two hours. On cooling, the separated solid can be filtered, washed with water and crystallized from acetic acid to provide the anti-ulcerative colitis compounds.

The anti-ulcerative colitis compound can be useful for treating ulcers. For example, the anti-ulcerative colitis compound can be an active agent in a pharmaceutical composition for treating ulcerative colitis. A pharmaceutical composition including the anti-ulcerative colitis compound can include one or more pharmaceutically acceptable carriers. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents and the like; for solid oral preparations, suitable carriers and additives include starches, sugars, diluents, granulating agents, lubricants, binders, disintegrating agents and the like. For parenteral use, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. Accordingly, the pharmaceutically acceptable carrier can include alcohol, dimethyl sulfoxide (DMSO), a physiological saline, a lipid based formulation, a liposomal formulation, a nanoparticle formulation, a micellar formulation, a water soluble formulation, a biodegradable polymer, an aqueous preparation, a hydrophobic preparation, a lipid based vehicle, or a polymer formulation.

The anti-ulcerative colitis compound or compositions thereof can be administered to a subject by any suitable route for treating ulcers and/or ulcerative colitis. Parenteral, otic, ophthalmic, nasal, inhalable, buccal, sublingual, enteral, topical, oral, peroral, and injectable dosage forms are particularly useful. Particular dosage forms include solid or liquid dosage forms. Exemplary suitable dosage forms include tablet, capsule, pill, caplet, troche, sache, solution, suspension, dispersion, vial, bag, bottle, injectable liquid, i.v. (intravenous), i.m. (intramuscular) or i.p. (intraperitoneal) administrable liquid and other such dosage forms known to the artisan of ordinary skill in the pharmaceutical sciences.

The amount of the anti-ulcerative colitis compound incorporated in a dose can be selected according to the examples provided herein and/or according to known principles of pharmacy. An effective amount or therapeutically effective amount of the anti-ulcerative colitis compound is specifically contemplated. By the term "effective amount", it is understood that, with respect to, for example, pharmaceuticals, a pharmaceutically effective amount is contemplated. A pharmaceutically effective amount is the amount or quantity of active ingredient which is enough for the required or desired therapeutic response, or in other words, the amount, which is sufficient to elicit an appreciable biological response when administered to a patient. The appreciable biological response, i.e., anti-ulcerogenic and/or anti-ulcerative colitis (UC) activities, can occur as a result of administration of single or multiple doses of an active substance. A dose may comprise one or more dosage forms. It will be understood that the specific dose level for any patient will depend upon a variety of factors including the indication being treated, severity of the indication, patient health, age, gender, weight, diet, pharmacological response, the specific dosage form employed, and other such factors. According to an embodiment, about 50 mg/kg to about 100 mg/kg of one or more of the anti-ulcerative colitis compounds can be orally administered on a daily basis to a subject in need thereof for a period of about 5 days to about 15 days.

The present teachings will be understood more readily by reference to the following examples, which are provided by way of illustration.

Example 1

Synthesis of 2-(4-Methylbenzamido) benzoic acid (Compound 2)

4-methylbenzoyl chloride (8.50 g, 0.05 mol) was added dropwise to a stirred solution of anthranilic acid (6.85 g, 0.05 mol) and triethylamine (2 mL) in dichloromethane (70 mL) and the reaction mixture was stirred at room temperature for two hours. The solvent was evaporated from the solution, under reduced pressure, to yield a solid acid amide product of 2-(4-methylbenzamido) benzoic acid, which has the structure:

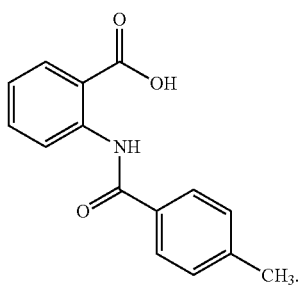 [SMILES: Cc1ccc(C(=O)Nc2ccccc2C(=O)O)cc1]

The separated solid was filtered, washed several times with water, dried and crystallized from ethanol.

Example 2

Synthesis of 2-p-tolyl-4H-3,1-benzoxazin-4-one (Compound 3)

A mixture of the 2-(4-methylbenzamido)benzoic acid (7.65 g, 0.03 mol) and acetic anhydride (7.5 g, 0.07 mol) was heated under reflux for five hours. The solvent was removed under reduced pressure. The residue was then triturated with water. The separated solid was collected by filtration, washed with water, and dried and crystallized from ethanol, yielding a benzoxazone derivative, 2-p-tolyl-4H-3,1-benzoxazin-4-one, which has the structure:

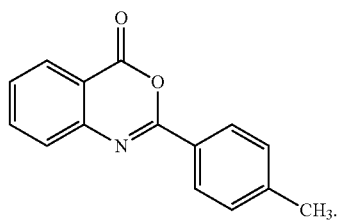 [SMILES: Cc1ccc(-c2nc3ccccc3c(=O)o2)cc1]

Example 3

Synthesis of 2-(4-methylphenyl)-3-amino-3H-quinazolin-4-one (Compound 4)

2-(4-methylphenyl)-3-amino-3H-quinazolin-4-one (Compound 4) was synthesized using three different methods. In the first method, a mixture of the 2-(4-methylphenyl)-4H-3,1-benzoxazin-4-one (1.18 g, 0.005 mol) (Compound 3) and 98% hydrazine hydrate (0.6 g, 0.018 mol) in ethanol (10 ml) was heated under reflux for 10 hours. The reaction mixture was then cooled and the separated solid was filtered and dried. The solid obtained was separated on a column using chloroform as eluent to provide Compound 4 in 15% yield. In the second method, a mixture of the benzoxazin-4-one (1.18 g, 0.003 mol) and 98% hydrazine hydrate (0.6 g, 0.018 mol) in n-butanol (10 mL) was heated under reflux for 10 hours. The reaction mixture was then cooled and the separated solid was filtered and dried. The solid obtained was separated on a column using chloroform as eluent to provide Compound 4 in 30% yield. In the third method, a mixture of the benzoxazin-4-one (1.18 g, 0.003 mot) and 98% hydrazine hydrate (0.6 g, 0.018 mol) was heated under reflux for three hours. On cooling, the separated solid was filtered, washed with water and crystallized from ethanol. The product obtained by these methods has the same physical constants. The 2-(4-methylphenyl)-3-amino-3H-quinazolin-4-one (Compound 4) has the following structure

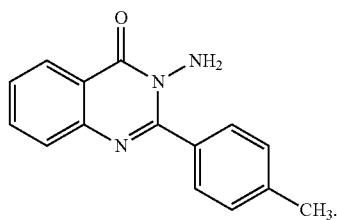 [SMILES: Cc1ccc(-c2nc3ccccc3c(=O)n2N)cc1]

Example 4

Synthesis of 3-substituted (arylideneamino)-2p-tolyl-3H-quinazolin-4-one (Compounds 5 & 6)

A mixture of 2-(4-methylphenyl)-3-amino-3H-quinazolin-4-one (Compound 4) (2.51 g, 0.01 mol) and aldehyde derivatives (0.01 mol) in acetic acid (20 mL) was heated under reflux for two hours to produce the anti-ulcerative colitis compound. The aldehyde derivatives included vanillin and 3,4,5-trimethoxy-benzaldehyde. On cooling, the separated solid was filtered, washed with water and crystallized from acetic acid to provide 3-[(4-hydroxy-3-methoxy-benzylidene)-amino]-2-p-tolyl-3H-quinazolin-4-one (Compound 5) and 2-p-tolyl-3-[3,4,5-trimethoxy-benzylidene-amino]-3H-quinazolin-4-one (Compound 6), having the following structures.

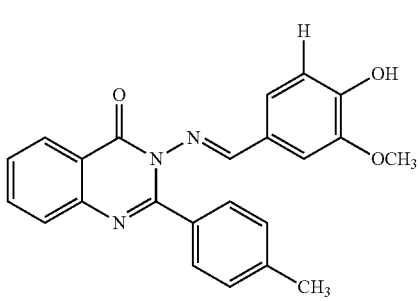

Compound 5 and

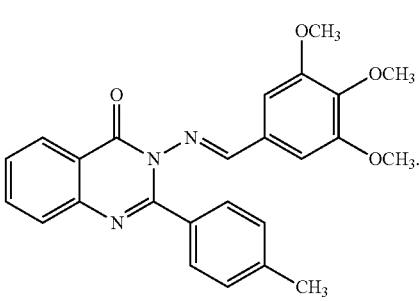

Compound 6

Compounds 5 and 6 produced by the above method were each tested using NMR spectroscopy. For Compound 5, the $^1$H and $^{13}$C NMR data are as follows: Yield, 85%; m.p. 192-194° C.; IR, υ (cm-1): 3385 (OH), 3045 (Ar—CH), 2941 (CH), 1668 (C=O). $^1$H NMR (CDCl3): δ 2.35 (s, 3H, CH3), 3.69 (s, 3H, OCH3), 5.29 (s, 1H, OH), 7.30-7.76 (m, 11H, Ar—H), 8.36 (s, 1H, N=CH). $^{13}$C NMR: 24.8 (CH3), 55.8 (OCH3), 114.9, 117.5, 120.2, 122.5, 122.9, 125.1, 126.3, 127.4, 128.0, 129.2, 133.8, 139.5, 143.7, 148.1, 151.8, 152.3, 159.8 (Ar—C), 167.2 (CO). MS m/z (Rel. Int.) 385 (M+, 100). Anal. (C23H19N3O3, 385.41) C, 71.67 (71.44); H, 4.97 (5.15); N, 10.90 (10.72).

For Compound 6, the $^1$H and $^{13}$C NMR data are as follows: Yield, 67%; m.p. 236-238° C.; IR, υ (cm−1): 3047 (Ar—CH), 2946 (CH), 1665 (C=O). NMR (CDCl3): δ 2.34 (s, 3H, CH3), 3.69 (s, 9H, 3OCH3), 7.30-7.76 (m, 10H, Ar—H), 8.39 (s, 1H, N=CH). $^{13}$C NMR: 24.5 (CH3), 56.1 (2OCH3), 55.6 (OCH3), 108.6, 120.4, 122.9, 125.6, 126.2, 127.5, 128.2, 128.9, 129.4, 133.7, 139.1, 141.7, 143.5, 150.3, 150.9, 152.2, 159.5 (Ar—C), 164.7 (CO). MS m/z (Rel. Int.) 429 (M+, 100). Anal. (C25H23N3O4, 429.46) C, 69.92 (70.11); H, 5.40 (4.66); N, 9.78 (9.64).

Example 5

Biological Activity

The anti-ulcerative colitis compounds were tested on Swiss albino mice of both genders (26-30 g), as well as male Wistar rats (180-200 g). The animals were housed in standard polypropylene cages with wire mesh tops and maintained under standard conditions (temperature of 23±1.0° C., humidity of 55±10%, 12 h light/12 h dark cycle). They were fed with a standard pellet diet with water ad libitum and were allowed to adapt to the laboratory environment for one week before experimentation.

In order to determine the oral median lethal dose ($LD_{50}$) of the anti-ulcerative colitis compound, the Swiss albino mice (in groups of six), received one of 50, 100, 500, or 1000 mg/kg doses of the target compound. Control animals received the pharmaceutical vehicle only and were kept under the same conditions. Signs of acute toxicity and the number of deaths per dose within 24 hours were recorded.

In order to examine the effect of the treatment compounds on ulcerative colitis, five groups of six rats were used. Two groups received compounds 5 and 6 at a dose of 50 mg/kg of body weight. Three other groups of animals were used, with two receiving water orally and the third receiving dexamesathone at a dose of 0.1 mg/kg orally, serving as control, control colitis and standard groups, respectively. All medications were administered for five successive days. Two hour after the last dose, ulcerative colitis was induced by slowly infusion of 2 mL (4%, v/v) of acetic acid in saline into the colon through a catheter. Two days after the induction of colitis, the animals were sacrificed and colonic segments (8 cm in length and 3 cm proximal to the anus) were excised, opened and were used for macroscopic scoring.

To assess colonic lesions, the colon specimens were weighted and the wet weight/length ratio was calculated for all of the animals. The specimens were examined under a dissecting microscope and mucosal lesions were quantified by the scoring system (0-5): 0=no damage, 1=local edema and inflammation without ulcers; 2=one ulcer without inflammation; 3=one to two ulcers with inflammation and lesion diameter <1 cm; 4=more than two ulcers with lesion diameter 1-2 cm; 5=severe ulceration with lesion diameter >2 cm.

Ulcer area was measured using a plane glass square. Each cell on the glass square was 1 $mm^2$ in area and the number of cells were counted and the ulcer area was determined for each colon. Ulcer index was measured by summing the lesion score and the ulcer area for each colon specimen. All values were expressed as mean±S.D. Statistical analysis was performed using SPSS 10. Statistical significance of differences between two means was assessed by unpaired student's T-test. Differences at $p<0.05$, 0.01, and 0.001 were considered statistically significant.

The male Wister rats were divided into two equal groups each having ten rats. The first group was left as a control and administered the vehicle orally, while the second group was orally administered Compounds 5 and 6 in a dose of 100 mg/kg for 15 days. After the examination period, 6 hours after the last dose blood samples were collected from the orbital plexus of rats, samples were left to clot at room temperature for 30 minutes and then centrifuged at 1000 rpm for 20 minutes. The collected sera were used for determination of the activity of both aspirate aminotransferase (AST) and alanine aminotransferase (ALT) as liver markers. Additionally, levels of blood urea and serum creatinine were also estimated as kidney markers.

It was found that Compounds 5 and 6, in doses up to 1000 mg/kg, did not produce any behavioral changes and/or mortality in mice. Therefore, they can be categorized as highly safe since substances possessing $LD_{50}$ higher than 5000 mg/kg are nontoxic.

The model of acetic acid-induced colitis shares many of the histologic features of ulcerative colitis in human beings, including mucosal edema and sub-mucosal ulceration. In rats of the control group, no abnormal changes were observed, suggesting that the handling procedure had no interference with the experimental outputs. Macroscopic damage parameters of the colon of the control colitis rats, two days after rectal infusion of acetic acid, revealed dark brown lesions, mucosal hyperemia, edema, erosion, and ulceration. The control colitis rats showed lesion score, ulcer area and ulcer index values of 4.7±0.89, 179.50±1.21 $mm^2$ and 183.5±2.26, respectively (see Table 1 below). The inflammatory changes of the intestinal tract were associated with a significant increase of wet weight/length of the colon specimens as an indicator of inflammation.

The prophylactic effect of Compounds 5 and 6 at a dose of 50 mg/kg on acetic acid-induced colitis in rats is also shown below in Table 1. Compounds 5 and 6, administrated orally to rats, showed a potent anti-ulcerative colitis activity. Compounds 5 and 6 at all tested doses induced a significant ($p<0.01$) decrease in ulcer score, ulcer area, ulcer index and weight/length of the colon specimens. The percent protection of control colitis was 51.2% and 61.8% for 3-[(4-hydroxy-3-methoxy-benzylidene)-amino]-2-p-tolyl-3H-quinazolin-4-one (Compound 5) and 2-p-tolyl-3-[3,4,5-trimethoxy-benzylidene-amino]-3H-quinazolin-4-one (Compound 6), respectively. However, the percent protection for dexamesathone (0.1 mg/kg) was 72.2%. The effect of Compounds 5 and 6 at a dose of 50 mg/kg were significantly ($p<0.01$) less effective than dexamesathone (0.1 mg/kg) in reducing all parameters.

TABLE 1

| | Effect of Compounds 5 and 6 on Acetic Acid-induced Colitis | | | |
|---|---|---|---|---|
| Groups | Lesion score (0-5) | Ulcer area ($mm^2$) | Ulcer index | Wet W/L (g/8 cm) |
| Normal control | 0.0 ± 0.0 | 0.0 ± 0.0 | 0.0 ± 0.0 | 0.41 ± 0.05 |
| Control colitis | 4.00 ± 0.89 | 179.50 ± 1.21 | 183.5 ± 2.26 | 0.83 ± 0.07 |
| Dexamethasone (0.1 mg/kg) | 1.83* ± 0.75 | 49.20* ± 1.47 | 51.00* ± 2.00 | 0.56* ± 0.05 |

TABLE 1-continued

Effect of Compounds 5 and 6 on Acetic Acid-induced Colitis

| Groups | Lesion score (0-5) | Ulcer area (mm$^2$) | Ulcer index | Wet W/L (g/8 cm) |
|---|---|---|---|---|
| Comound 5 (50 mg/kg) | 2.33* ± 0.52 | 87.17*@ ± 1.17 | 89.50*@ ± 1.22 | 0.72*@ ± 0.03 |
| Compound 6 (50 mg/kg) | 2.170* ± 0.75 | 68.00*@ ± 1.55 | 70.17*@ ± 1.72 | 0.62* ± 0.04 |

*Significantly different from control colitis at p <0.01.
@Significantly different from dexamesathone at p <0.01.

Both the liver and kidney functions were not affected, as there is no significant difference between the control and test groups in all experiments (at the 0.05 level of probability), as shown below in Table 2. These results show that compound 5 and 6 do not result in hepatotoxic manifestation. Additionally, no apparent nephrotoxic manifestations were recorded.

TABLE 2

Effect of Compounds 5 and 6 on Liver and Kidney Functions

| Groups | ALT(U/l) | AST(U/l) | Blood Urea (mg/dl) | Creatinine (mg/dl) |
|---|---|---|---|---|
| Control | 42.49 ± 0.37 | 60.77 ± 0.37 | 70.50 ± 1.36 | 0.88 ± 0.02 |
| Compound 5 (50 mg/kg) | 38.67 ± 0.22 | 63.23 ± 0.39 | 65.50 ± 1.9 | 0.85 ± 0.02 |
| Compound 6 (50 mg/kg) | 38.67 ± 0.22 | 63.23 ± 0.39 | 65.50 ± 1.9 | 0.85 ± 0.02 |

Data are expressed as mean ± SD, n = 10

It is to be understood that the present invention is not limited to the embodiments described above, but encompasses any and all embodiments within the scope of the following claims.

We claim:

1. A compound of 2-p-tolyl-3-[3,4,5-trimethoxy-benzylidene-amino]-3H-quinazolin-4-one comprising the structural formula:

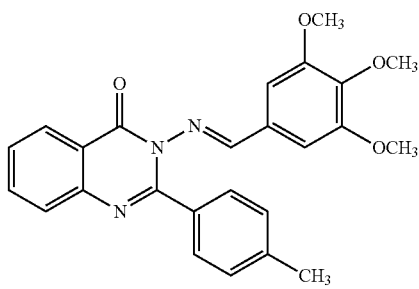

2. A pharmaceutical composition comprising the compound according to claim 1 and a pharmaceutically acceptable carrier.

3. A method for treating ulcerative colitis, comprising administering to a patient in need thereof a therapeutically effective amount of the compound of claim 1.

4. The method of treating ulcerative colitis as recited in claim 3, wherein the therapeutically effective amount comprises from about 50 mg/kg to about 100 mg/kg.

5. The method of treating ulcerative colitis as recited in claim 3, wherein the compound is administered orally.

6. A method for preparing the anti-ulcerative colitis compound according to claim 1, comprising the steps of:

reacting anthranilic acid with 4-toluoyl chloride to form a first solution;

evaporating a solvent from the first solution to yield 2-(4-methylbenzamido)benzoic acid;

refluxing the 2-(4-methylbenzamido)benzoic acid with acetic anhydride to yield 2-p-tolyl-4H-3,1-benzoxazin-4-one;

boiling the 2-p-tolyl-4H-3,1-benzoxazin-4-one with hydrazine hydrate in the presence of absolute ethanol to produce 2-(4-methylphenyl)-3-amino-3H-quinazolin-4-one; and treating the 2-(4-methylphenyl)-3-amino-3H-quinazolin-4-one with an aldehyde derivative to produce the compound.

7. The method for preparing the anti-ulcerative colitis compound according to claim 6, wherein the aldehyde is vanillin.

8. The method for preparing the anti-ulcerative colitis compound according to claim 6, wherein the aldehyde is 3,4,5-trimethoxy-benzaldehyde.

* * * * *